United States Patent [19]
Chen et al.

[11] Patent Number: 5,686,471
[45] Date of Patent: Nov. 11, 1997

[54] DIHYDROBENZOFURAN AND RELATED COMPOUNDS USEFUL AS ANTI-INFLAMMATORY AGENTS

[75] Inventors: Zhuoliang Chen, Fairfield; John Michael Janusz, West Chester, both of Ohio

[73] Assignee: The Procter & Gamble Company, Cincinnati, Ohio

[21] Appl. No.: 595,120

[22] Filed: Feb. 1, 1996

[51] Int. Cl.$^6$ .............. A61K 31/34; C07D 405/06; C07D 407/06
[52] U.S. Cl. .............. 514/337; 514/406; 514/443; 514/444; 514/469; 544/333; 546/284.1; 548/202; 548/214; 548/236; 549/9; 549/15; 549/58; 549/49; 549/53; 549/345; 549/355; 549/405; 549/462
[58] Field of Search .............. 549/9, 15, 58, 549/60, 49, 53, 345, 355, 405, 462; 546/284.1; 548/364.4; 514/337, 466, 443, 444, 469

[56] References Cited

U.S. PATENT DOCUMENTS

| | | | |
|---|---|---|---|
| 4,470,440 | 9/1984 | Thor | 144/193 C |
| 4,670,457 | 6/1987 | Doria et al. | 514/470 |
| 4,849,428 | 7/1989 | Dobson et al. | 549/307 |
| 4,857,516 | 8/1989 | Terao et al. | 514/100 |
| 4,966,907 | 10/1990 | Caldwell et al. | 514/337 |
| 4,966,973 | 10/1990 | Goto | 546/269 |
| 4,975,457 | 12/1990 | Rupprecht et al. | 514/469 |
| 5,091,533 | 2/1992 | Belanger et al. | 544/318 |
| 5,380,877 | 1/1995 | Chandraratna et al. | 549/60 |

FOREIGN PATENT DOCUMENTS

| | | |
|---|---|---|
| 53-005178 | 1/1978 | Japan. |
| WO9012007 | 10/1990 | WIPO. |
| WO9107396 | 5/1991 | WIPO. |
| WO9114674 | 10/1991 | WIPO. |

OTHER PUBLICATIONS

M.L. Hammond, Kopa I.E., Zambias R.A., Caldwell C.G., Boger J., Baker, F. Bach T., Luell S., & Macintyre D.E. "1,3-Dihydro-5-benzofuranols as Antioxidant-Based Inhibitors of Leukotriene Biosynthesis", *J. Med. Chem.*, vol. 32 (1989), pp. 1006–1020.

O. deMontellano, Correia, P.R., Correia, M.A.; "Suicidal Destruction of Cytochrome P-450 During Oxidative Drug Metabolism", *Ann. Rev. Pharmacol. Toxicol.*, vol. 23 (1983), pp. 481–503.

J.K. Chakabarti, Eggleton R.J., Gallagher P.T., Harvey J., Hicks T.A., Kitchen E.A., & Smith C.W.; "5–Acyl–3–Substituted–Benzofuran–2(3H)–Ones as Potential Anti–Inflammatory Agents", *J. Med. Chem.*, vol. 30 (1987), pp. 1663–1668.

*Primary Examiner*—Bernard Dentz
*Attorney, Agent, or Firm*—Mary Pat McMahon; Karen F. Clark; Jacobus C. Rasser

[57] ABSTRACT

A compound having the structure:

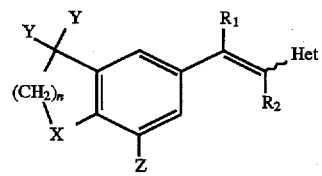

wherein
- (a) n is from about 1 to about 3;
- (b) X is selected from the group consisiting of O, S, SO, or $SO_2$;
- (c) Y is independently hydrogen or straight, branched or cyclic alkyl or aralkyl having from 1 to about 3 carbon atoms; or the Y's are bonded together to form an alkanyl ring having from 3 to about 7 atoms;
- (d) Z is hydrogen or straight, branched or cyclic alkyl having from 3 to about 10 atoms other than hydrogen;
- (e) $R_1$ and $R_2$ are each independently hydrogen or straight, branched or cyclic alkyl, unsubstituted or substituted, carboxyl, carboxamido, alkoxycarbonyl or alkylcarbonyl; and
- (f) Het is a heteroaryl group comprising one or more rings containing from about 5 to about 8 atoms in the rings and wherein at least one ring has at least one heteroatom selected from O, N, or S, pharmaceutical compositions comprising such compounds, and methods of treating inflammation or pain using such compounds.

19 Claims, No Drawings

DIHYDROBENZOFURAN AND RELATED COMPOUNDS USEFUL AS ANTI-INFLAMMATORY AGENTS

TECHNICAL FIELD

The subject invention relates to nonsteroidal anti-inflammatory drugs, particularly to substituted dihydrobenzofuran and related compounds.

BACKGROUND OF THE INVENTION

Certain dihydrobenzofuran compounds and other compounds structurally related thereto have been found to have significant disease altering activities. Such compounds, processes for making them, and uses for them are disclosed in the following references: U.S. Pat. No. 4,670,457 issued to Doria, Romeo & Como on Jun. 2, 1987; U.S. Pat. No. 4,849,428 issued to Dobson, Loomans, Matthews & Miller on Jul. 18, 1989; Japanese Patent Publication No. 53-005178 of Yoshitomi Pharm. Ind. KK published Jan. 1, 1978; Hammond, M. L., I. E. Kopka, R. A. Zambias, C. G. Caldwell, J. Boger, F. Baker, T. Bach, S. Luell & D. E. MacIntyre, "2,3-Dihydro-5-benzofuranols as Antioxidant-Based Inhibitors of Leukotriene Biosynthesis", *J. Med. Chem.*, Vol. 32 (1989), pp. 1006–1020; Ortiz de Montellano, P. R & M. A. Correia, "Suicidal Destruction of Cytochrome P-450 during Oxidative Drug Metabolism", *Ann. Rev. Pharmacol. Toxicol.*, Vol. 23 (1983), pp. 481–503; Chakrabarti, J. K., R. J. Eggleton, P. T. Gallagher, J. Harvey, T. A. Hicks, E. A. Kitchen, and C. W. Smith, "5-Acyl-3-substituted-benzofuran-2(3H)-ones as Potential Anti-inflammatory Agents", *J. Med. Chem.*, Vol. 30 (1987), pp. 1663–1668.

It is an object of the subject invention to provide compounds which have effective anti-inflammatory, analgesic and/or anti-oxidant activity.

It is a further object of the subject invention to provide such compounds which cause few adverse side effects.

It is also an object of the subject invention to provide methods for treating inflammation and/or pain using the subject compounds.

SUMMARY OF THE INVENTION

The subject invention compounds having the structure:

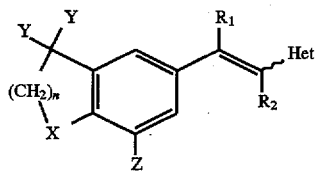

wherein (a) n is from 1 to about 3;

(b) X is selected from the group consisiting of O, S, SO, or $SO_2$;

(c) Y is independently hydrogen or straight, branched or cyclic alkyl or aralkyl having from 1 to about 4 carbon atoms; or the Y's are bonded together to form an alkanyl ring having from 3 to 7 atoms;

(d) Z is hydrogen or straight, branched or cyclic alkyl alkyl having from 3 to about 10 atoms other than hydrogen;

(e) $R_1$ and $R_2$ are each independently hydrogen or straight, branched or cyclic alkyl, carboxyl, carboxamido, alkoxycarbonyl or alkylcarbonyl; and (f) Het is a heteroaryl group comprising one or more rings containing from about 5 or 6 8 atoms in each ring and wherein at least one ring has at least one heteroatom selected from O, N, or S.

DETAILED DESCRIPTION OF THE INVENTION

As used herein, unless otherwise indicated, "alkyl" or "alkanyl" means a straight, branched or cyclic hydrocarbon chain, saturated or unsaturated, unsubstituted or substituted. Preferred alkyls are $C_1$–$C_{10}$; more preferred are $C_1$–$C_8$; especially preferred are $C_1$–$C_4$. Preferred alkyls are straight chain. Preferred branched alkyl have one or two branches, preferably one branch. Preferred cyclic alkyl are monocyclic or are a straight chain with a monocyclic terminus. Preferred alkyl are saturated. Unsaturated alkyl have one or more double bonds or/and one or more triple bonds. Preferred unsaturated alkyl have one or two double bonds or one triple bond, more preferably one double bond. Preferred alkyl are unsubstituted. Preferred substituted alkyl are mono-, di-, or trisubstituted, more preferably monosubstituted. Preferred alkyl substituents include halo, hydroxy, oxo, alkoxy (e.g., methoxy, ethoxy, propoxy, butoxy, pentoxy), aryloxy (e.g., phenoxy, chlorophenoxy, tolyloxy, methoxyphenoxy, benzyloxy, alkyloxycarbonylphenoxy, acyloxyphenoxy), acyloxy (e.g., propionyloxy, benzoyloxy, acetoxy), carbamoyloxy, carboxy, mercapto, alkylthio, acylthio, arylthio (e.g., phenylthio, chlorophenylthio, alkylphenylthio, alkoxyphenylthio, benzylthio, alkyloxycarbonylphenylthio), aryl (e.g., phenyl, tolyl, alkyloxphenyl, alkyloxycarbonylphenyl, halophenyl), heterocyclyl, heteroaryl, amino (e.g., amino, mono- and di- $C_1$–$C_3$ alkanylamino, methylphenylamino, methylbenzylamino), $C_1$–$C_3$ alkanylamido, ureido, N'-alkylureido, N',N'-dialkylureido, N',N",N-trialkylureido, guanidino, N'-alkylguanidino, N',N"-dialkylguanidino, or alkoxy carbonyl.

As used herein, "alkoxy" means-O-alkyl.

As used herein, "aryl" means a moiety having an unsubstituted or substituted aromatic ring having 6 to about 10 carbon atoms. Preferred aryl are phenyl and naphthyl; most preferred aryl is phenyl. Preferred aryl are unsubstituted. Preferred substituted aryl are mono-, di-, or trisubstituted, more preferably monosubstituted. Preferred aryl substituents include hydroxy, mercapto, halo, methyl, ethyl and propyl.

As used herein, "heteroaryl" means a moiety having an aromatic ring having 5 or 6 ring atoms including from 1 to 5 carbon atoms and from 1 to 4 heteroatoms selected from O, S and N. Preferred heteroaryls have 1 or 2 heteroatoms in the ring. The heteroaryl ring may be substituted or unsubstituted. Specific preferred heteroaryls include 2 or 3-furyl, 2 or 3-thienyl, 2 or 3-pyrrolyl either unsubstituted or alkylsubstituted on nitrogen, 2, 4, or 5 thiazolyl, 2, 4, or 5-oxaxolyl, 2, 4, or 5-imidazolyl either unsubstituted or alkyl-substituted on nnitrogen, 3, 4, or 5-isoxazolyl, 3, 4, or 5-isothiazolyl, 3, 4, or 5-pyrazolylunsubstituted or alkyl-substituted on nitrogen, 2 or 5-oxdiazolyl, 2 or 5-thiadiazolyl, triazolyl, tetrazolyl, pyridyl, pyrimidinyl, pyrazinyl, indolyl, quinolyl, isoquinolyl. Most preferred is 3-pyridyl. Preferred substituted heterocycles are mono-, di-, or trisubstitued, more preferably monosubstituted. Preferred heterocycle substitutents include alkyl, halo, hydroxy, alkoxy, thio, nitro, amino, amido, ureido, guanidino, thiocarbamamido, thioureido.

As used herein, "halo" means fluoro, chloro, bromo or iodo. Preferred halo are fluoro, chloro and bromo; more preferred are chloro and bromo, especially chloro.

Compounds

The subject invention involves compounds having the following structure:

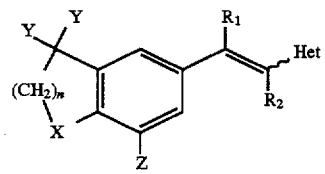

wherein (a) n is from 1 to about 3;

(b) X is selected from the group consisting of O, S, SO, or $SO_2$;

(c) Y is independently hydrogen or straight, branched or cyclic alkyl having from 1 to about 3 carbon atoms; or the Y's are bonded together to form an alkanyl ring having from 3 to about 7 atoms;

(d) Z is hydrogen or straight, branched or cyclic alkyl having from 3 to about 10 atoms other than hydrogen;

(e) $R_1$ and $R_2$ are each independently hydrogen or straight, branched or cyclic alkyl, unsubstituted or substituted, carboxyl, carboxamido, alkoxycarbonyl or alkylcarbonyl; and (f) Het is a heteroaryl group comprising one or more rings containing from about 5 to about 8 atoms in the rings and wherein at least one ring has at least one heteroatom selected from O, N, or S.

In the above structure, each Y is independently selected from hydrogen, straight or branched alkanyl having from 1 to about 4 carbon atoms, and cyclic alkyl having about 3 carbon atoms, cyclopropyl, or the Y's are bonded together to form a cyclic alkanyl ring having from 3 to about 7 carbon atoms in the ring. Each Y is preferably hydrogen, methyl, ethyl or cyclopropyl; more preferably hydrogen or methyl; most preferably methyl. Preferably both Y's are the same. When the Y's are bonded together to form a cyclic ring, the ring is preferably cyclopropyl, cyclobutyl or cyclopentyl, more preferably cyclopropyl.

In the above structure, Z is selected from branched or cyclic alkyl, and phenyl, or benzyl, Z having from 3 to about 10 atoms other than hydrogen. Z is preferably saturated.

Z is preferably branched alkanyl having from about 3 to about 8 carbon atoms, more preferably from about 4 to about 6 carbon atoms. Z is preferably branched alkanyl having 2 or more branches, more preferably 2 branches. Preferred branched alkanyl Z include t-butyl, neopentyl, isopropyl; most preferred is t-butyl. Preferred cyclic alkanyl Z include cyclopropyl, cyclobutyl, cyclopentyl, cyclohexyl, cycloheptyl. Also preferred Z is unsubstituted phenyl or benzyl.

In the above structure $R_1$ and $R_2$ are each independently hydrogen or straight, branched or cyclic alkyl, unsubstituted or substituted, carboxyl, carboxamido, alkoxycarbonyl or alkylcarbonyl. Examples of carboxamido groups include unsubstituted, monosubstituted and disubstituted carboxamides such as carboxamido, N-methyl-carboxamido, N,N-dimethylcarboxamido and other N-alkyl and N,N-dialkylcarboxamido groups. Examples of alkoxycarbonyl groups include, methoxycarbonyl, ethoxycarbonyl, tert-butoxycarbonyl, and benzyloxycarbonyl. Examples of alkylcarbonyl groups include, methylcarbonyl, ethylcarbonyl, tert-butylcarbonyl, and benzylcarbonyl.

In the above structure Het is a heteroaryl group having one or more rings having 5 or 6 ring atoms in each ring including from 1 to 5 carbon atoms and at least one ring containing from 1 to 4 heteroatoms selected from O, S and N. Preferred heteroaryls have 1 or 2 heteroatoms in the ring. Specific preferred heterocycles include 2 or 3-furyl, 2 or 3-thienyl, 2 or 3-pyrrolyl either unsubstituted or alkylsubstituted on nitrogen, 2, 4, or 5 thiazolyl, 2, 4, or 5-oxazolyl, 2, 4, or 5-imidazolyl either unsubstituted or alkyl-substituted on nitrogen, 3, 4, or 5-isoxazolyl, 3, 4, or 5-isothiazolyl, 3, 4, or 5-pyrazolyl unsubstituted or alkyl-substituted on nitrogen, 2 or 5-oxdiazolyl, 2 or 5-thiadiazolyl, triazolyl, tetrazolyl, pyridyl, pyrimidinyl, pyrazinyl, indolyl, quinolyl, isoquinolyl. Heteroaryls are unsubstituted or substituted, preferably unsubstituted. Preferred substituted heteroaryls are mono-, di-, or trisubstitued, more preferably monosubstituted. Preferred heteroaryls substitutents include alkyl, halo, hydroxy, alkoxy, thio, nitro, amino, amido, ureido, guanidino, thiocarbamamido, thioureido.

Preferred compounds of the subject invention are included in the following table:

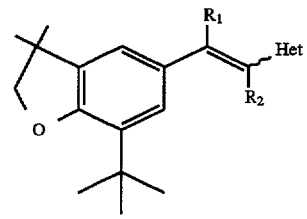

| Compound No. | R1 | R2 | Het |
|---|---|---|---|
| 1 | H | CO2H | 2-thienyl |
| 2 | H | H | 2-thienyl |
| 3 | H | H | 5-methyl-pyrazol-3-yl |
| 4 | H | H | 3-pyridyl |

In order to determine and assess pharmacological activity, testing of the subject compounds in animals is carried out using various assays known to those skilled in the art. The anti-inflammatory activity of the subject compounds can be conveniently demonstrated using an assay designed to test the ability of the subject compounds to antagonize the local edema which is characteristic of the inflammatory response. Examples of such known tests include the rat carrageenan edema test, the oxazolone-induced inflamed mouse ear test, and the mouse arachadonic acid-induced inflamed ear test. Analgesic activity may be tested in art-known models such as the phenylbenzoquinone-induced writhing test in mice, and the Randall & Selitto test in rats. Another useful art-known test is the rat adjuvant arthritis test which is a useful model for assessing anti-inflammatory activity, anti-arthritic and anti-resorptive activity in a chronic, rather than an acute, model.

These and other appropriate tests for pharmacological activity are disclosed and/or referred to in U.S. Pat. No. 4,130,666 issued to Moore on Dec. 19, 1978; U.S. Pat. No. 4,431,656 issued Feb. 14, 1984 to Katsumi, et al.; U.S. Pat. No. 4,440,784 issued to Katsumi, et al. on Apr. 3, 1984; Japanese Patent Application 85/54315 of Katsumi, et al., published Mar. 28, 1985; European Patent Application No. 0,059,090 of Yamanuchi Pharmaceutical Company Ltd., published Sep. 1, 1982; Opas, E. V., R. J. Bonney & J. L. Humes, "Prostaglandin and Leukotriene Synthesis in Mouse Ears Inflamed by Arachadonic Acid", *The Journal of Investigative Dermatology*, Vol. 84, No. 4 (1985), pp. 253–256; Swingle, K. F., R. L. Bell & G. G. I. Moore, "Anti-inflammatory Activity of Antioxidants", *Anti-inflammatory* and *Antirheumatic Drugs*, Vol. III, Chapter 4, K. D. Rainsford, ed., CRC Press, Inc., (1985), pp. 105–126; Adamkiewicz, V. W., W. B. Rice & J. D. McColl, "Antiphlogistic Effect of Trypsin in Normal and in Adrenalectomized Rats", *Canadian Journal of Biochemistry & Physiology*, Vol. 33 (1955), pp. 332–339; Sellye, H., "Further Studies Concerning the Participation of the Adrenal Cortex in the Pathogenesis of Arthritis", *British Medical Journal*, Vol. 2 (1949), pp. 1129–1135; and Winter, C. A., E. A. Risley & G. W. Nuss, "Carrageenan-Induced Edema in Hind Paw of the Rats as an Assay for Antiinflammatory Drugs" *Proceedings of Society of Experimental Biology and Medicine*, Vol. 111 (1962), pp. 544–547; Otterness, I., & M. L. Bliven, "Laboratory Methods for Testing Nonsteroidal Antiinflammatory Drugs", *Nonsteroidal Antiinflammatory Drugs*, Chapter 3, J. G. Lombardino, ed., John Wiley & Sons, Inc. (1985), pp. 111–252. Hitchens, J. T., S. Goldstein, L. Shemano & J. M. Beiler, "Analgesic Effects of Irritants in Three Models of Experimentally-Induced Pain", *Arch. Int. Pharmacodyn.*, Vol. 169, No. 2 (1967) pp. 384–393; Milne, G. M. & T. M. Twomey, "The Analgesic Properties of Piroxicam in Animals and Correlation with Experimentally Determined Plasma Levels", *Agents and Actions*, Vol. 10, No. ½ (1980), pp. 31–37; Randall, L. O. & J. J. Selitto, "A Method for Measurement of Analgesic Activity on Inflamed Tissue", *Arch. Int. Pharmacodyn.*, Vol. 111, No. 4 (1957), pp. 409–419; Winter, C. A. & L. Faltaker, "Nociceptive Thresholds as Affected by Parenteral Administration of Irritants and of Various Antinociceptive Drugs", *J. Pharmacol. Exp. Ther.*, Vol. 148, No. 3 (1965), pp. 373–379; the disclosure of all these references are incorporated herein by reference.

Many anti-inflammatory drugs, particularly non-steroidal anti-inflammatory drugs (NSAIDs) cause undesirable gastrointestinal side effects, especially when dosed perorally; such side effects may include ulcers and erosions. These side effects, which are often asymptomatic, can become serious enough to require hospitalization and can even be lethal. Compounds of the subject invention generally cause fewer such gastrointestinal side effects compared to other NSAIDs. Some compounds of the subject invention are even gastroprotective, protecting the stomach and intestines from ulcers and erosions, particularly those caused by ethanol or other NSAIDs.

Certain NSAIDs, when dosed systematically, cause an undesirable increase in systemic levels of certain liver enzymes. Compounds of the subject invention generally cause little or no liver enzyme side effects.

Compounds useful in the subject invention can be made using the following general reaction scheme:

Styrylpyrazoles are prepared via an isoxazolylmethyl carbanion approach. The carbanion, generated by regioselective deprotonation at the 5-methyl position of 3,5-dimethylisoxazole by n-BuLi, is reacted with aryl aldehyde (I), (prepared from the arylbromide), to give the alcohol addition product. This compound then undergoes dehydration to form the styrylisoxazole. Conversion of the styrylisoxazole to the styrylpyrazole is carried out following Kobayashi's hydrogenolysis procedure (J. Chem. Soc. Chem. Comm. 1982, 877) using Mo(CO)₆ followed by pyrazole ring formation using hydrazine.

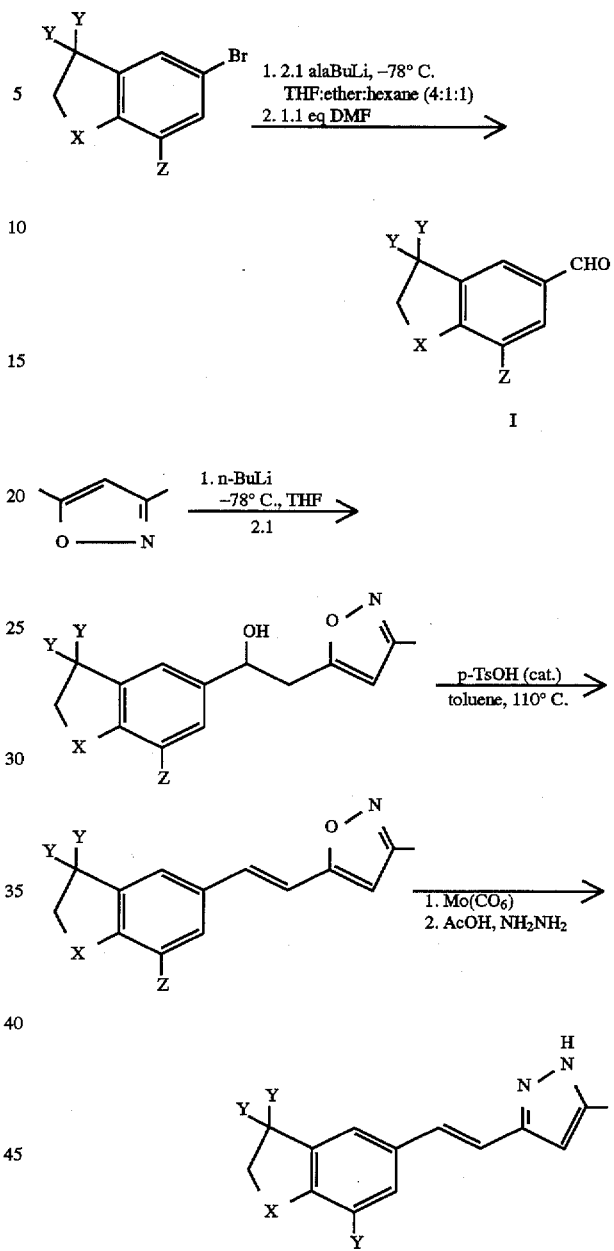

Styrylthiophenes are prepared via two routes. Knoevenagel reaction between aryl aldehyde and 2-thiophenecarboxylic acid in hot piperidine gives the styryl acid. Decarboxylation is realized by heating with copper at 250° C. to provide styrylthiophene as a mixture of the E/Z isomers. The E-isomer is separated from the E/Z mixture by recrystallization.

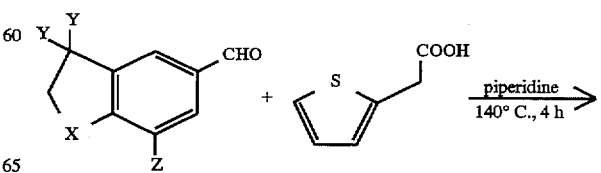

-continued

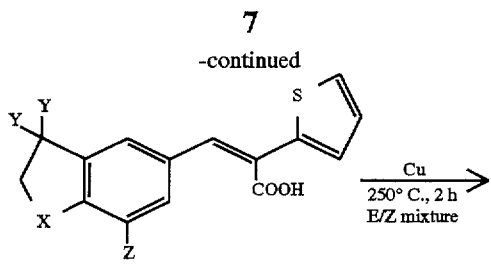

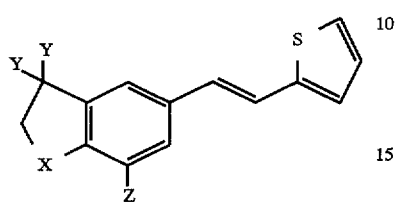

Styrylthiophenes can also be prepared via the Wittig reaction. An aryl aldehyde or its sodium a-hydroxy sulfonate generated from reaction with NaHSO₃, reacts with the ylide generated from 2-thiophenemethyl triphenylphosphonium chloride and t-BuOK to form a mixture of E/Z isomers of styrylthiophenes. Stereoselective formation of the E isomer is accomplished via a Wittig-Homer reaction using ethyl 2-thiophenemethylphosphonate (prepared from 2-thiophenemethanol via the thiophenemethylchloride) as the ylide source.

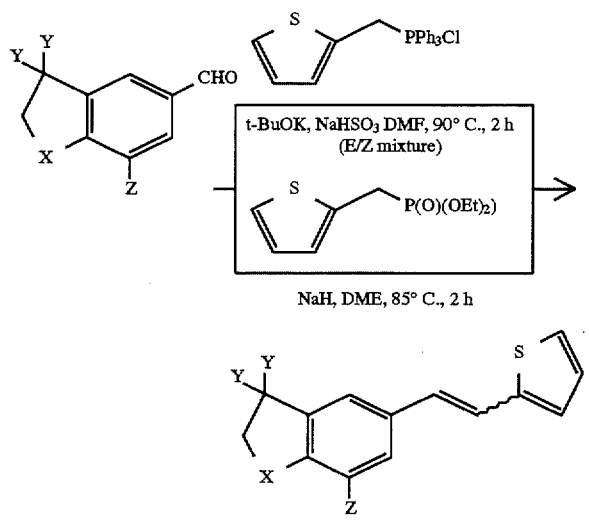

Wittig reactions also provide the styrylpyridine compounds. Reaction of the aldehyde with 3-picolylmethyltriphenylphosphonium chloride in the presence of sodium amide forms a mixture of the E-olefin and the Z-olefin which are separable by silica gel chromatography.

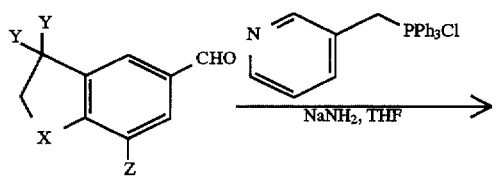

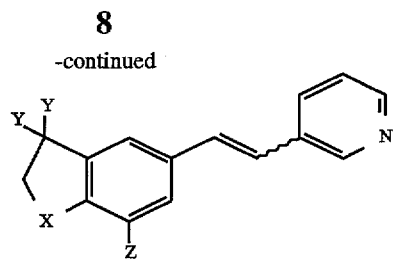

SYNTHESIS EXAMPLES

The following non-limiting examples provide further information regarding synthesis of the subject compounds.

Example 1

E-3-(7'-tert-Butyl-2',3'-dihydro-3',3'-dimethylbenzo[b]furan-5'-yl)-2-(2"-thiophene)propenoic Acid To a mixture of (7-tert-butyl-2,3-dihydro-3,3-dimethylbenzo[b]furan-5-yl)carboxaldehyde (1.064 g, 4.59 mmol) and 2-thiopheneacetic acid (978 mg, 6.88 mmol) is added piperidine (1.5 mL). The mixture is heated at 140° C. (oil bath temperature) for 4 h, cooled to room temperature, quenched with water and extracted with ethyl acetate (3×). The organic layer is washed with brine (2×), dried over anhydrous $Na_2SO_4$ and concentrated by rotary evaporation to give brown semi-solid. Silica gel chromatography (5% MeOH in $CH_2Cl_2$) of this crude product provides the title comound as a yellow solid (543 mg, 34.0%), mp: 183°–185° C.

Example 2a

5-[E-2'-(2"-Thiophene)ethenyl]-7-tert-butyl-2,3-dihydro-3,3-dimethylbenzol[b]furan A mixture of the acid from example 1 (1.081 g, 3.034 mmol) and copper powder (385 mg, 6.02 mmol) in $CH_2Cl_2$ (5 mL) is heated at 250° C. for 2 h. The residue is taken up with $CH_2Cl_2$ and filtered through a silica gel pad with 1/1 of $CH_2Cl_2$/hexane washing. Concentration of the filtrate via rotary evaporation gives an oily material which contains a 85/15 mixture of the E/Z olefins by $^1H$ NMR analysis. Further purification via silica gel chromatography (10–20% $CH_2Cl_2$ in hexane) affords a pure E/Z olefin mixture (510 mg, 53.8%) from which recrystallization from a $CH_2Cl_2$/hexane mixture (1 mL/4 mL) provides pure E-olefin (283 mg, 29.9%) as a white solid, mp: 113.5°–115° C.

Example 2b

5-[E-2'-(2"-Thiophene)ethenyl]-7-tert-butyl-2,3-dihydro-3,3-dimethylbenzo[b]furan Step 1: 2-Thiophenemethylchloride To 2-thiophenemethanol (9.5 mL, 100 mmol) in $CH_2Cl_2$ (100 mL) at 0° C. is added thionyl chloride (14.6 mL, 200 mmol), followed by pyridine (9.7 mL, 120 mmol). The mixture is stirred at room temperature for 30 min and concentrated via rotary evaporation. The resulting brown oil is filtered through a silica gel pad with 5% ether in hexane washing to give, after evaporation of the filtrate, the title compound as an orange oil (6.50 g, 48.9%) which is stored in the cold and in the dark, and is used in the next step within a week.

Step 2: Diethyl 2'-thiophenemethylphosphonate

A mixture of 2-thiophenemethylchloride (1.1 g, 8.3 mmol) and triethylphosphite (2.07 mL, 12.1 mmol) is heated at 130° C. for 4 h. The resulting mixture is subjected to Kugelrohr distillation to remove the excess triethyl phosphite (50° C./0.005 mm) followed by the title phosphonate as a clear oil (90°–130° C./0.005 mm, 1.00 g, 51.8%).

Step 3: 5-[E-2'-(2"-Thiophene)ethenyl]-7-tert-butyl-2,3-dihydro-3,3-dimethylbenzo[b]furan A mixture of (7-tert-butyl-2,3-dihydro-3,3-dimethylbenzo[b]furan-5-yl)carboxaldehyde (90%, 8.763 g, 33.95 mmol) and the phosphonate from step 2 (8.04 mL, 40.7 mmol) and NaH (60% in mineral oil, 3.26 g, 81.5 mmol, washed with hexane 3×, and dried in vacuo prior to use) in anhydrous DME (Aldrich, 68 mL) is heated at reflux under nitrogen for 2 h (violent evolution of $H_2$ started at ca. 5–10 min of heating, good ventilation should be ensured). Upon completion of the reaction the mixture is quenched carefully with water and extracted with ether (3×). The organic layer is washed with brine, dried over anhydrous $Na_2SO_4$ and concentrated via rotary evaporation. The resulting residue, of which $^1H$ NMR analysis shows no trace of the Z-olefin, is recrystallized from a 1/1 mixture of $CH_2Cl_2$/hexane to provide the title compound (7.054 g, 65.9%) as a white solid. Silica gel chromatography (5% $CH_2Cl_2$ in hexane) of the mother liquid affords more of the title compound (2.041 g, total, 85.5% yield).

Example 3

5-[E-2'-(2"-Thiophene)ethenyl]-7-tert-butyl-2,3-dihydro-3,3-dimethylbenzo[b]thiophene A mixture of (7-tert-butyl-2,3-dihydro-3,3-dimethylbenzo[b]thiophene-5-yl)-carboxaldehyde (500 mg, 2.01 mmol) and phosphonate from step 2 of example 2 (476 mL, 2.41 mmol) and NaH (60% in mineral oil, 193 mg, 4.83 mmol, washed with hexane 3×, and dried in vacuo prior to use) in anhydrous DME (Aldrich, 4 mL) is heated at reflux under nitrogen for 2 h (violent evolution of $H_2$ started at ca. 5–10 min of heating, good ventilation should be ensured). Upon completion of the reaction the mixture is quenched carefully with water and extracted with ether (3×). The organic layer is washed with brine, dried over anhydrous $Na_2SO_4$ and concentrated via rotary evaporation. The resulting residue, of which is recrystallized from a 1/1 mixture of $CH_2Cl_2$/hexane to provide the desired compound (408 mg, 61.8%) as a white solid.

Example 4

5-[E-2'-(5"-Methyl-1H-pyrazol-3"-yl)ethenyl]-7-tert-butyl-2,3-dihydro-3,3-dimethylbenzo[b]furan Step 1: 1-(7'-tert-Butyl-2',3'-dihydro-3',3'-dimethylbenzo[b]furan-5'-yl)-2-(3"-methylisox-azol-5"-yl)ethanol To 3,5-dimethylisoxazole (1.47 mL, 15.0 mmol) in THF (15 mL) at −78° C. is added n-BuLi (1.47M in hexane, 10.0 mL, 14.7 mmol). The mixture is stirred at −78° C. for 2 h. To the resulting yellow solution is added at −78° C. dropwise aldehyde 7-tert-butyl-2,3-dihydro-3,3-dimethylbenzo[b]furan-5-yl)-formaldehyde (3.48 g, 15.0 mmol) in THF (60 mL). The reaction mixture is stirred at room temperature for 5 h, and then concentrated via rotary evaporation. The residue is partitioned between water and ethyl acetate (3×). The organic layer is washed with brine (3×), dried over anhydrous $Na_2SO_4$, and concentrated through rotary evaporation to give a brown oil. Silica gel chromatography afforded the desired alcohol as a thick yellow oil which then solidifies as a white solid (4.355 g, 88.2%): top: 71°–72° C.

Step 2: 5-[E-2'-(3"-Methylisoxazol-5"-yl)ethenyl]-7-tert-butyl-2,3-dihydro-3,3-dimethylbenzo[b]furan To alcohol from step 1 (3.230 g, 9.80 mmol) in toluene (50 mL) is added p-toluenesulfonic acid monohydrate (9 mg). The mixture is heated at reflux for 2 h with continuous removal of solvent via a Dean-Stark refluxing condensor. The mixture is concentrated. The residue is purified through silica gel chromatography (65% $CH_2Cl_2$ in hexane), followed by recrystallization from hexane/$CH_2Cl_2$ (15 mL/1 mL) to provide a 15/1 mixture, as determined by $^1H$ NMR analysis, of E/Z-isomers (2.28 g, 74.8%): mp: 121.5°–123° C.

Step 3: 5-[E-2'-(5"-Methyl-1H-pyrazol-3"-yl)ethenyl]-7-tert-butyl-2,3-dihydro-3,3-dimethyl-benzo[b]furan To a mixture of isoxazole from step 2 (1.543 g, 4.96 mmol) and molybdenum hexacarbonyl (982 mg, 3.72 mmol) is added acetonitrile (58 mL) and water (89 mL, 4.96 mmol). The mixture is heated at reflux for 14 h and concentrated via rotary evaporation. To the residue is added methanol (30 mL) and 2N HCl (0.8 mL) until pH=1. The mixture is stirred for 5 h and concentrated again, then treated with water (30 mL) and neutralized with 1N NaOH. Ethyl acetate and brine are added. The separated aqueous layer is extracted with ethyl acetate (3×). The combined organic layer is filtered through a silica gel pad with chloroform washing. The organic filtrate is concentrated and the residue is taken up with ethyl acetate, filtered through a silica gel pad with ethyl acetate washing. The organic layer is treated with acetic acid (78 mL) and 97% hydrazine (0.779 mL, 24.8 mmol). The mixture is stirred for 20 h, followed by removal of acetic acid via vacuum evaporation. The residue is washed with water and filtered. The resulting brown cake is purified by silica gel chromatography (1% methanol in $CH_2Cl_2$) followed by recrystallization from hexane to provide the title compound (645 mg, 41.9%) as a light yellow solid: mp: 145°–147° C.

Example 5

5-[E-2'-(3"-Pyridinyl)ethenyl]-7-tert-butyl-2,3-dihydro-3,3-dimethylbenzo[b]furan To a mixture of 3-picolyl triphenylphosphonium chloride (4.87 g, 12.5 mmol, prepared from 3-picolyl chloride and triphenylphosphine) and sodium amide (90%, 541 mg, 12.5 mmol) is added THF (32 mL). The mixture is stirred at room temperature for 2 h and then cooled to −78° C. To this pink slurry at −78° C. is added 7-tert-butyl-2,3-dihydro-3,3-dimethylbenzo[b]furan-5-yl)carboxaldehyde (1.16 g, 5 mmol) in THF (10 mL). The mixture was stirred at −78° C. for 10 min and then at room temperature for 2 h. The solvent is removed via rotary evaporation. The residue is taken up with ether, and filtered. The residue is washed with ether (2×). The combined organic layer is concentrated, leaving a residue which contains a 40/60 mixture of the E/Z double bond isomers. Separation of the isomers is performed via silica gel chromatography (20–25% ethyl acetate in hexane) to afford the Z isomer (788 mg, 51.3%) and the E isomer (580 mg, 37.7%, mp: 72°–74° C.), both as white solids.

COMPOSITIONS

Compositions of the subject invention comprise a safe and effective amount of the subject compounds, and a pharmaceutically-acceptable carrier. As used herein, "safe and effective amount" means an amount of a compound sufficient to significantly induce a positive modification in the condition to be treated, but low enough to avoid serious side effects (at a reasonable benefit/risk ratio), within the scope of sound medical judgment. A safe and effective amount of a compound will vary with the particular condition being treated, the age and physical condition of the patient being treated, the severity of the condition, the duration of the treatment, the nature of concurrent therapy, the particular pharmaceutically-acceptable carrier utilized, and like factors within the knowledge and expertise of the attending physician.

Compositions of the subject invention preferably comprise from about 0.1% to about 99.9% by weight of a compound, more preferably from about 20% to about 80%, and most preferably from about 40% to about 70%.

In addition to the compound, the compositions of the subject invention contain a pharmaceutically-acceptable carrier. The term "pharmaceutically-acceptable carrier", as used herein, means one or more compatible solid or liquid filler diluents or encapsulating substances which are suitable for administration to a human or lower animal. The term "compatible", as used herein, means that the components of the composition are capable of being commingled with the subject compound, and with each other, in a manner such that there is no interaction which would substantially reduce the pharmaceutical efficacy of the composition under ordinary use situations. Pharmaceutically-acceptable carriers must, of course, be of sufficiently high purity and sufficiently low toxicity to render them suitable for administration to the human or lower animal being treated.

Some examples of substances which can serve as pharmaceutically-acceptable carriers or components thereof are sugars, such as lactose, glucose and sucrose; starches, such as cornstarch and potato starch; cellulose and its derivatives, such as sodium carboxymethyl cellulose, ethyl cellulose, cellulose acetate; powdered tragacanth; malt; gelatin; talc; solid lubricants, such as stearic acid, magnesium stearate; calcium sulfate; vegetable oils, such as peanut oil, cottonseed oil, sesame oil, olive oil, corn oil and oil of theobroma; polyols such as propylene glycol, glycerin, sorbitol, mannitol, and polyethylene glycol; alginic add; emulsifiers, such as the Tweens®; wetting agents such as sodium lauryl sulfate; coloring agents; flavoring agents, excipients; tableting agents; stabilizers; antioxidants; preservatives; pyrogen-free water; isotonic saline; and phosphate buffer solutions.

The choice of a pharmaceutically-acceptable carrier to be used in conjunction with a subject compound is basically determined by the way the compound is to be administered.

If the subject compound is to be injected, it is preferably injected non-intravenously; the preferred pharmaceutically-acceptable carrier is sterile, physiological saline, with blood compatible suspending agent, the pH of which has been adjusted to about 7.4. Such injectable compositions preferably comprise from about 1% to about 50% of the subject compound, more preferably from about 5% to about 25%, also preferably from about 10 mg to about 600 mg of the subject compound per dose.

Suitable pharmaceutically-acceptable carriers for topical application include those suited for use in lotions, creams, gels and the like. Topical compositions preferably contain from about 1% to about 50% of an emollient, more preferably from about 5% to about 25% of an emollient. Such topical compositions preferably comprise from about 0.1% to about 50%, of the subject compound, more preferably from about 0.5% to about 10%, also preferably from about 5 mg to about 3500 mg per dose.

The preferred mode of administering the subject compound is perorally. The preferred unit dosage form is therefore tablets, capsules and the like, comprising a safe and effective amount of the compound, which is preferably from about 5 mg to about 3500 mg, more preferably from about 10 mg to about 1000 mg, and most preferably from about 25 mg to about 600 mg. The pharmaceutically-acceptable carriers suitable for the preparation of unit dosage forms for oral administration are well-known in the art. Their selection will depend on secondary considerations like taste, cost, and shelf stability, which are not critical for the purposes of the subject invention, and can be made without difficulty by a person skilled in the art.

Many of the subject compounds are hydrophobic. If it is desired to provide an aqueous-based composition or a composition soluble in or miscible with aqueous media, a solubilizing agent may be included in the composition. Non-limiting examples of such solubilizing agents include polyethylene glycol, propylene glycol, ethanol, and polyoxyethylene (35) castor oil.

Particularly preferred oral composition carriers suitable for compositions of the subject invention are disclosed in U.S. Pat. No. 5,189,066 of Kelm & Bruns, issued Feb. 23, 1993, entitled "Pharmaceutical Compositions of Tebufelone", and U.S. Pat. No. 5,281,420 of Kelm & Dobrozsi, issued Jan. 25, 1994, entitled "Solid Dispersion Compositions of Tebufelone", hereby incorporated herein by reference.

METHODS

Another aspect of the subject invention is methods for treating or preventing diseases characterized by inflammation by administering a safe and effective amount of a subject compound to a human or lower animal in need of such treatment. The term "diseases characterized by inflammation", as used herein, means conditions which are known to involve inflammation, and may include conditions such as arthritis (e.g., rheumatoid arthritis, osteoarthritis, psoriatic arthritis, juvenile arthritis, Reiter's syndrome, infectious arthritis, and ankylosing spondylitis, systemic lupus, erythematosus and gout), as well as the presence of inflammation whether or not it is associated with an identifiable disease. Diseases characterized by inflammation further may include inflammation in the oral cavity (e.g., inflammation associated with gingivitis or periodontal disease); inflammation in the gastrointestinal tract, (e.g., inflammation associated with ulcers and irritable bowel disease); inflammation associated with dermatological diseases (e.g., psoriasis, acne, and other skin inflammation); inflammation associated with the respiratory tract (e.g., asthma, bronchitis, and allergies); and inflammation in the central nervous system (e.g., Alzheimer's disease).

Another aspect of the subject invention is methods for treating or preventing pain by administering a safe and effective amount of a subject compound to a human or lower animal in need of such treatment. Pain which can be treated or prevented by administering the subject compounds may include peripheral pain, menstrual pain, dental pain, and lower back pain. Another aspect of the subject invention is methods for preventing oxidative damage at inflammatory sites by administering a safe and effective amount of a subject compound to a human or lower animal in need of such treatment. While not limited to a particular mechanism, it is believed that the subject compounds inhibit leukotriene synthesis, thereby decreasing neutrophil accumulation at an inflammatory site.

Another aspect of the subject invention is methods for treating or preventing gastric or duodenal ulcers or erosions by administering a safe and effective amount of a subject compound to a human or lower animal in need of such treatment. In particular, such ulcers or erosions caused by ethanol or non-steroidal antiinflammatory drugs (NSAIDs) can be treated and/or prevented by administration of preferred subject compounds.

Appropriate tests for determining the gastrointestinal safety or gastroprotective or gastric healing properties of the subject compounds are known.

Methods for determining acute gastrointestinal safety are disclosed and/or referred to in the following references: Unangst, P. C., G. P. Shrum, D. T. Connor, R. D. Dyer, and D. J. Schrier, "Novel 1,2,4-Oxadiazoles and 1,2,4-Thiadiazoles as Dual 5-Lipoxygenase and Cyclooxygenase Inhibitors", *J. Med. Chem.*, Vol. 35 (1992), pp. 3691–3698; and Segawa, Y., O. Ohya, T. Abe, T. Omata, et al., "Anti-inflammatory, Analgesic, and Antipyretic Effects and Gastrointestinal Toxicity of the New Anti-inflammatory Drug N-{3-[3-(piperidinylmethyl)phenoxy]propyl}carbamoylmethylthio]ethyl 1-(p-chlorobenzoyl)5-Methoxy-2methyl-3-indolylacetate", *Arzneim.-Forsch./ Drug Res.*, Vol. 42 (1992), pp. 954–992. In the methods disclosed therein, stomachs of the animals are typically examined two hours after dosing a compound. Methods for determining subchronic gastrointestinal safety are disclosed and/or referred to in the following references: Melarange, R., C. Gentry, et al., "Anti-inflammatory and Gastrointestinal Effects of Nabumetone or Its Active Metabolite, 6-Methoxy-2-naphthylacetic Acid (6MNA)", *Dig. Dis. Sci.*, Vol. 37 (1992), pp. 1847–1852; and Wong, S., S. J. Lee, et al., "Antiarthritic Profile of BF-389—A Novel Anti-inflammatory Agent With Low Ulcerogenic Liability", *Agents Actions*, Vol. 37 (1992), pp. 90–91.

Methods for determining acute gastroprotection are disclosed and/or referred to in the following reference: Playford, R. J., D. A. Versey, S. Haldane, M. R. Alison, and J. Calan, "Dose-dependent Effects of Fentanyl on Indometharin-induced Gastric Damage", *Digestion*, Vol. 49 (1991), pp. 198–203. In the method disclosed therein, female Lewis rats (130–175 g) are dosed perorally with the subject compound (40 mg/kg b.i.d.) or vehicle at 2 hours and immediately before administration of a gastric damaging dose of indomethacin. The rats are sacrificed 4 hours later by $CO_2$ asphyxiation. Gastric corpus damage (millimeters of hemorrhagic lesions) is measured by digitized imaging.

The preferred mode of administration of the subject compounds is peroral, but other known methods of administration are contemplated as well, e.g., dermatomucosally (for example, dermally, rectally and the like), and parenterally (for example, by subcutaneous injection, intramuscular injection, intraarticular injection, intravenous injection and the like). Ocular administration and inhalation are also included. Thus specific modes of administration include, without limitation, peroral, transdermal, mucosal, sublingual, intranasal, intramuscular, intravenous, intraperitoneal, subcutaneous, and topical administration.

Preferred doses of the subject compounds range from about 0.2 mg/kg to about 70 mg/kg, more preferably from about 0.5 mg/kg to about 12 mg/kg. Preferred injectable doses comprise from about 0.1 mg/kg to about 10 mg/kg of the subject compound. Preferred topical doses comprise from about 1 mg/cm$^2$ to about 200 mg/cm$^2$ of the subject compound applied to the skin surface. Preferred peroral doses comprise from about 0.5 mg/kg to about 50 mg/kg, more preferably from about 1 mg/kg to about 20 mg/kg, more preferably still from about 2 mg/kg to about 10 mg/kg, of the subject compound. Such doses are preferably administered from about once to about six times daily, more preferably from about twice to about four times daily. Such daily doses are preferably administered for at least one week, also preferably for at least two weeks, also preferably at least one month, also preferably for at least 2 months, also preferably for at least 6 months, 1 year, 2 years, or more.

COMPOSITIONS AND METHOD EXAMPLES

The following non-limiting examples illustrate the subject invention.

Example A

Pharmaceutical compositions in the form of tablets are prepared by conventional methods, such as mixing and direct compaction, formulated as follows:

| Ingredient | Quantity (mg per tablet) |
| --- | --- |
| Compound 1 | 200 |
| Microcrystalline Cellulose | 100 |
| Sodium Starch Glycollate | 30 |
| Magnesium Stearate | 3 |

When administered orally two times daily, the above composition significantly reduces the inflammation in a patient suffering from rheumatoid arthritis. A significant benefit is also achieved by twice daily administration of this composition to a patient suffering from osteoarthritis.

Example B

A pharmaceutical composition in capsule form is prepared by conventional methods, formulated as follows:

| Ingredient | Quantity (mg per capsule) |
| --- | --- |
| Compound 4 | 200 |
| Lactose | To fill to volume of capsule |

The above capsule administered orally once a day substantially reduces the symptomology of a patient afflicted with rheumatoid arthritis or osteoarthritis.

Example C

A pharmaceutical composition in liquid form is prepared by conventional methods, formulated as follows:

| Ingredient | Quantity |
| --- | --- |
| Compound 2 | 200 mg. |
| EtOH | 4 ml |
| Methyl cellulose | 0.4 mg |
| Distilled water | 76 ml |
| Tween 80 | 1.6 ml |

50 ml of the above composition administered perorally once a day substantially reduces the symptoms of a patient afflicted with rheumatoid arthritis or osteoarthritis.

Example D

A pharmaceutical composition in liquid form is prepared by conventional methods, formulated as follows:

| Ingredient | Quantity |
| --- | --- |
| Microcrystalline (micronoized) Compound 3 | 200 mg |
| Avicel (microcrystalline cellulose) | 50 mg |
| Tween 80 | 1.6 ml |
| Methyl cellulose | 0.4 mg |
| Deionized water | 80 ml |

50 ml of the above composition administered perorally twice a day substantially reduces the symptoms of a patient afflicted with rheumatoid arthritis or osteoarthritis.

While particular embodiments of the subject invention have been described, it would be obvious to those skilled in the art that various changes and modifications to the compositions disclosed herein can be made without departing from the spirit and scope of the invention. It is intended to cover, in the appended claims, all such modifications that are within the scope of this invention.

What is claimed is:

1. A compound having the structure:

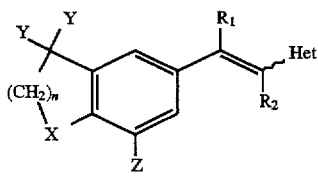

wherein
(a) n is from 1 to about 3;
(b) X is selected from the group consisiting of O, S, SO, or $SO_2$;
(c) Y is independently hydrogen or unsubstituted straight, branched alkyl or cycloalkyl having from 1 to about 3 carbon atoms; or the Y's are bonded together to form a cycloalkyl ring having from 3 to about 7 atoms;
(d) Z is hydrogen or straight, branched or cyclic alkyl having from 3 to about 10 atoms other than hydrogen; benzyl or phenyl;
(e) $R_1$ and $R_2$ are each independently hydrogen or straight, branched alkyl or cycloalkyl, unsubstituted or substituted, carboxyl, carboxamido, alkoxycarbonyl or alkylcarbonyl; and
(f) Het is a heteroaryl group comprising one or more rings containing from about 5 to about 8 atoms in the rings and wherein at least one ring has at least one heteroatom selected from O, N, or S.

2. The compound of claim 1 wherein X is oxygen and $R_1$ and $R_2$ are hydrogen, methyl or carboxyl.

3. The compound of claim 1 wherein each Y is independently selected from the group consisting of hydrogen, methyl and ethyl; and Z is selected from the group consisting of unsubstituted $C_4$–$C_6$ branched alkanyl having 2 branches, unsubstituted $C_3$–$C_6$ cycloalkanyl, and unsubstituted phenyl.

4. The compound of claim 3 wherein $R_1$ is hydrogen, both Y are methyl, and Z is t-butyl.

5. The compound of claim 3 wherein $R_1$ is hydrogen or methyl, and $R_2$ is $C_1$–$C_6$ straight or single-branched alkyl or straight alkyl with a terminal cyclic alkyl, saturated or unsaturated with one double bond between non-terminal carbon atoms, or $C_3$–$C_6$ cycloalkanyl or carboxyl.

6. The compound of claim 5 wherein X is oxygen, and Het is selected from the group consisting of 2 or 3-furyl, 2 or 3-thienyl, 2 or 3-pyrrolyl either unsubstituted or alkylsubstituted on nitrogen, 2, 4, or 5 thiazolyl 2, 4 or 5-oxazolyl 2, 4 or 5-imidazolyl either unsubstituted or alkyl-substituted on nitrogen, 3, 4, or 5-isoxazolyl, 3, 4, or 5-isothiazolyl, 3, 4, or 5-pyrazolyl unsubstituted or alkyl-substituted on nitrogen, 2 or 5-oxadiazolyl, 2 or 5-thiadiazolyl, triazolyl, tetrazolyl, pyridyl, pyrimidinyl, pyrazinyl, indolyl, quinolyl, isoquinolyl.

7. The compound of claim 6 wherein both Y are methyl, and Z is t-butyl.

8. The compound of claim 3 wherein R1 is hydrogen and R2 is hydrogen or —COOH.

9. The compound of claim 8 wherein both Y are methyl, and Z is t-butyl.

10. The compound of claim 9 wherein X is oxygen, and $R_2$ is hydrogen.

11. The compound of claim 10 wherein n is one and Het is is selected from the group consisting of 2-thienyl, 5-methyl-pyrazol-3-yl, or 3-pyridyl.

12. The compound of claim 11 wherein $R_2$ is hyrdrogen and Het is 2-thienyl.

13. The compound of claim 11 wherein $R_2$ is —COOH— and Het is selected from the group consisting of 2-thienyl, 5-methyl-pyrazol-3-yl, or 3-pyridyl.

14. A composition comprising a compound of claim 1 and a pharmaceutically-acceptable carrier.

15. A method of treating inflammation or pain comprising administation, to a human or lower animal in need of such treatment, of a safe and effective amount of a compound of claim 1.

16. A method of treating arthritis comprising daily peroral administration, to a human in need of such treatment, of from about 1 mg/kg to about 20 mg/kg of a compound of claim 1.

17. A composition comprising a compound of claim 11 and a pharmaceutically-acceptable carrier.

18. A method of treating inflammation or pain comprising administation, to a human or lower animal in need of such treatment, of a safe and effective amount of a compound of claim 11.

19. A method of treating arthritis comprising daily peroral administration, to a human in need of such treatment, of from about 1 mg/kg to about 20 mg/kg of a compound of claim 11.

* * * * *